United States Patent [19]
Mojena

[11] Patent Number: 5,353,805
[45] Date of Patent: Oct. 11, 1994

[54] AID FOR USE BY WOMEN IN DISCHARGE OF BODILY WASTES

[76] Inventor: Gregory L. Mojena, Calle 10 B7-1, Sabana Gardens, P.R. 00983

[21] Appl. No.: 166,013

[22] Filed: Dec. 14, 1993

[51] Int. Cl.⁵ .............................................. A61B 5/00
[52] U.S. Cl. .................................. 128/761; 128/760; 604/346
[58] Field of Search ..................... 128/760, 761, 767; 604/346, 356; 383/8, 9, 34

[56] References Cited

U.S. PATENT DOCUMENTS

| | | | |
|---|---|---|---|
| 976,883 | 11/1910 | Keagy | 128/761 X |
| 3,575,225 | 4/1971 | Muheim | 604/356 X |
| 3,964,111 | 6/1976 | Packer | |
| 4,305,161 | 12/1981 | Diaz | |
| 4,453,938 | 6/1984 | Brendling | 604/346 |
| 4,500,314 | 2/1985 | Brendling | 604/346 |
| 4,608,046 | 8/1986 | Towfigh | |
| 4,681,573 | 7/1987 | McGovern et al. | |
| 4,696,067 | 9/1987 | Woodward | 128/761 X |
| 4,757,751 | 6/1988 | Reno | |
| 4,937,890 | 7/1990 | Tafur | |
| 5,009,236 | 4/1991 | Brothers | 128/761 |

*Primary Examiner*—Sam Rimell
*Attorney, Agent, or Firm*—Oblon, Spivak, McCleland, Maier & Neustadt

[57] ABSTRACT

An aid for use by women in discharge of bodily wastes while standing erect. The aid includes tongs having legs engageable with seams at the open end of a flexible waste receiving bag. The legs are pivoted together at their inner ends and each leg has fixed thereto a handle with the leg and handle of each tong part being on the same side of the pivot whereby movement of the handles towards each other moves the legs apart and vice versa, the handles being urged apart by a spring. The size of the bag opening can be adjusted by the tongs to minimize accidents. One of the legs carries an outwardly open channel for engaging a leg opening of panties to move the panties clear of the relevant region as the bag is opened for use. The invention includes structure for the mounting of either a urine bag or a defecation bag.

9 Claims, 4 Drawing Sheets

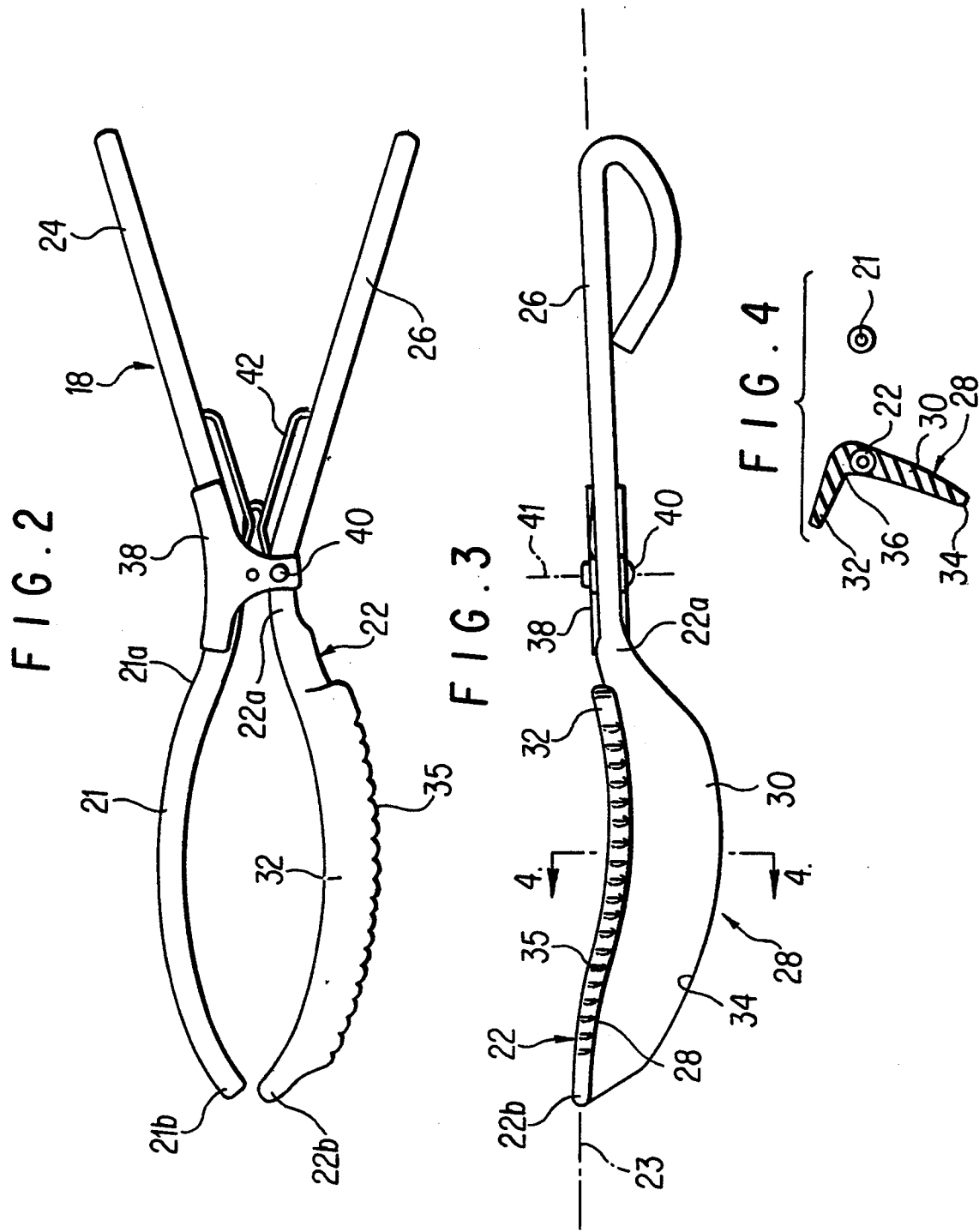

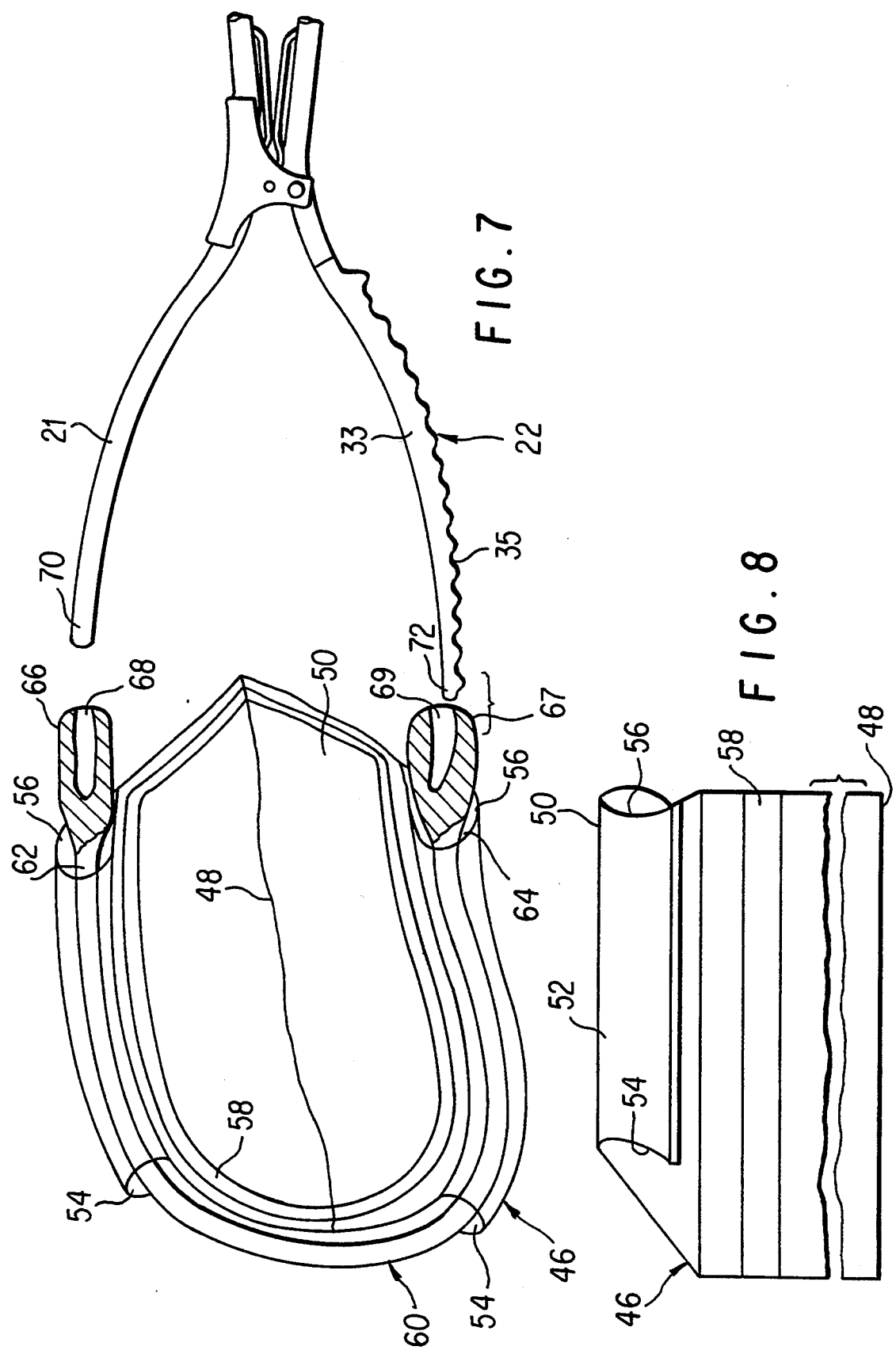

AID FOR USE BY WOMEN IN DISCHARGE OF BODILY WASTES

FIELD OF THE INVENTION

This invention relates to aids for use by women in the discharge of bodily wastes while standing erect. Though the invention is particularly adapted for use by women and is described in connection with such use, it will be apparent that under certain circumstances it can be used to advantage by men and such use is to be considered as being within the purview of the invention.

BACKGROUND OF THE INVENTION

Because women universally discharge bodily wastes in a seated position but many women are reluctant to sit on the toilet seats in public lavatories for fear of disease, there has been a recognized need for supplying women with alternatives to sitting on toilet seats. Thus the prior art has devised funnel-like devices which women can manually hold in place while standing erect and which have outlets for directing urine into a toilet bowl or elsewhere. Many of these prior devices are made of flimsy sheet material, usually paper treated so as to be temporarily waterproof, while still being disposable by flushing down a toilet. Not only are these devices difficult to hold in place but they usually require that the user clamp the device in place with her fingers and if the unit is not properly positioned, the results can be decidedly unpleasant.

The patent to Diaz No. 4,305,161 attempts to address this problem by the provision of a substantially rigid wish-bone shaped support frame having legs joined together at one end by a handle and which may be inserted into the open ended seams at the open upper end of a bag. With this arrangement, the user's finger's are separated to a certain extent from the danger zone but, because the legs of the frame are fixed with respect to each other, the user still has the problem of locating the frame in the proper position, with the same bad results if it should be mis-located.

The principal object of the present invention is to reduce the likelihood of mis-location of a urinary aid while providing means for positioning the user's fingers even further away from the danger zone than prior art devices.

A subsidiary object of the invention is to provide a urinary aid for women which enables the unit to be used without the necessity for a woman to remove her panties.

Another object of the invention is to provide a urinating aid for women which can be converted to a defecating aid.

SUMMARY OF THE INVENTION

The invention comprises the combination of a bag and tongs whereby an open end of the bag can be adjusted to a degree which largely eliminates the problem of mis-location and other problems associated with the single-size openings of prior art devices.

An important feature of the invention resides in constructing one of the legs of the tongs in the shape of an outwardly opening L-shaped channel arranged to engage the hem of the leg opening of a woman's panties such that as the legs of the tongs are spread to open the bag to completely cover the appropriate bodily region, the panty leg hem is pushed clear of that region thus eliminating the necessity for the woman to remove her panties entirely as would almost otherwise certainly be required.

Lastly, the tongs which are suited to aiding in urination can also be converted to a defecation aid by connecting the socket ends of a flexible U-shaped rod carrying an open topped bag to the outer ends of the tong legs. The size of the bag opening is easily controlled by the tongs and the bag can also be optimally positioned by the tongs with a minimum chance of accident, and also, panties may be moved to one side as explained above.

The invention will be better understood when the following detailed description is read in conjunction with the accompanying drawings wherein:

BRIEF DESCRIPTION OF THE DRAWINGS

FIG. 2 is a top plan view of the tongs of the invention;

FIG. 3 is a side elevational view of the tongs of FIG. 2;

FIG. 4 is a vertical cross sectional view taken substantially on the line 4—4 of FIG. 3;

FIG. 7 is a broken plan view of the tongs and an adapter for converting the invention to a defecation aid; and FIG. 8 is a broken side elevational view of a defecation bag.

Referring now to FIG. 1, the invention is there shown as it appears when ready for use as a urination aid. The invention comprises a waterproof bag 10, desirably of transparent plastic material, which has at its upper end an adjustable opening 12 having on either side thereof a pair of substantially parallel seams 14, 15 which are open at their respective inner ends 16, 17. For reasons that will become apparent one seam 15 must be large enough to accommodate an enlarged leg of the tongs, and both seams 14, 15 may be of this size and both may be open at both ends in order to minimize experimentation by the user in joining the bag and tongs.

Figure 1:
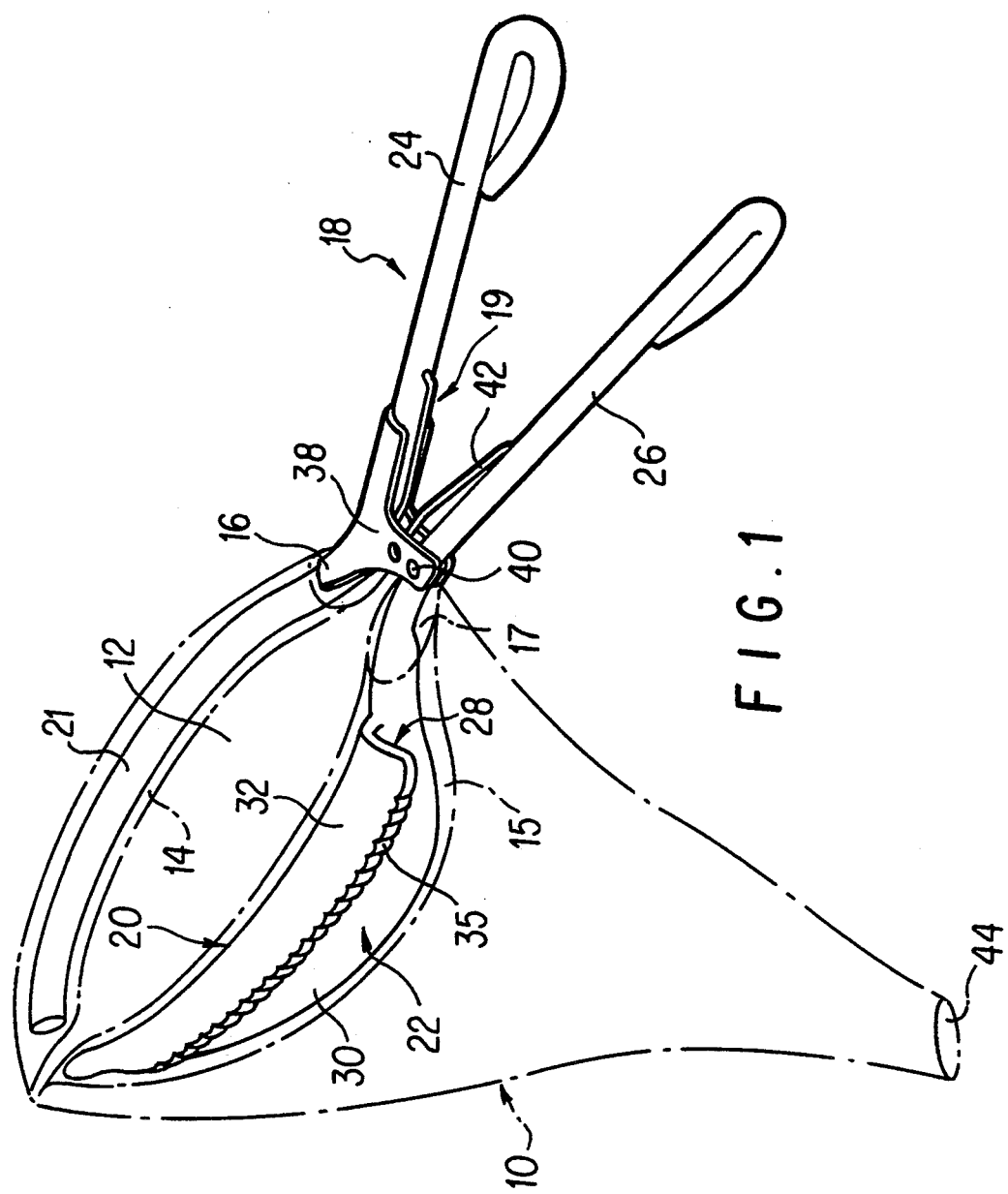
FIG. 1 is a perspective view of tongs with bag attached for use as a urination aide.

The numeral 18 designates a pair of tongs having a pair of legs 21, 22 relatively movable in substantially a common plane 23 (FIG. 3). The legs have inner ends 21a, 22a and free outer ends 21b, 22b, which are respectively insertable into the respective open ends 16, 17 of the bag seams 14, 15. Manually operable means, such as the handles 24, 26 are integral with the respective inner ends 21a, 22a of the legs 21, 22 for controlling the movement of the legs 21, 22 toward and away from each other for adjusting the size of the opening 12 of the bag 10 when the legs of the tongs are received in the respective seams 14, 15.

Though it is believed to be entirely novel to provide tongs having legs of equal cross sectional, say round, dimensions for controlling the size of the bag opening to ensure that the relevant region of the anatomy is properly covered and with a minimum chance of misalignment as can occur with prior urination aids, the present invention includes a marked improvement over prior art devices wherein the one leg 22 of the tongs may include an elongated outwardly opening channel 28, as best seen in FIG. 4. The channel 28 is of generally inverted L-shape in cross section having a relatively long depending arm 30 substantially perpendicular to the plane of movement 23 of the tong legs; and a shorter arm 32 at substantially right angles to the arm 30 and substantially parallel to plane 23. The channel 28 may be separately molded to the leg 22 of the tongs as is evident in FIG. 4 though the entire leg 22 including the channel 28 can be manufactured in its entirety as a separate unit. As can be seen in FIG. 4, the leg 30 of channel 28 is slightly outwardly curved in cross section and, as seen in FIG. 3, has a fin-like configuration in elevation, which is to say, it has a curved lower edge 34 whereby, when the user is wearing panties and the tongs with bag in place, is inserted between her legs, when the handles 24, 26 are manipulated to spread the legs of the tongs, the outer edge 35 of the arm 32 of the channel 28 slides under the seam of the adjacent leg opening of the panties. The other leg 20 of the tongs, being anchored on or in abutment with the inner thigh of the woman's other leg, provides a reaction base for the channel, with the intervening bag being no impediment to the entire operation. As the material of the panty leg gathers, it crowds into the bight 36, see FIG. 4, between the channel arms 30, 32. Desirably, the edge 35 of the arm 32 is serrated as shown at 37 to minimize the possibility of pinching pubic hair between the arm and the engaged hem of the panty hose. The foregoing will become clearer as the operation of the unit is described below in conjunction with FIGS. 5 and 6.

Turning now to FIGS. 1, 2 and 3 the invention includes novel construction of the tongs 18. As can be seen in these figures, the inner end 21a of leg 21 of the tong carries a bracket 38 intermediate its handle 24 and leg 21 and extending in the direction of the other tong half which is pivotally connected intermediate its handle 26 and leg to the bracket 38 by a pivot pin 40 defining a common pivotal connection whose axis 41 is substantially perpendicular to the plane of movement 23 of the tong legs.

As can be seen in the drawings, the handle and leg of each tong half are on the same side of the axis 41 of the pivot pin 40 Thus when the handles 24, 26 are moved towards or away from each other the legs move in the opposite direction. A spring 42 between the handles 24, 26 biases the handles apart from each other and the legs towards each other. As can best be understood from FIG. 2, the legs 21, 22, handles 24, 26 and pivotal connection 40 are arranged relative to each other that when the free outer ends 21b, 22b of the legs are positioned to be closer to each other, as in FIG. 2, the handles are positioned to be further from each other and vice versa.

The bag 10 may be closed at the bottom for the purpose of retaining expelled urine as may be desirable, for example, where urine is to be subjected to laboratory testing. On the other hand, the bag may be funnel shaped as seen in FIG. 1 and provided at its lower end with an opening 44 whereby a woman may drain expelled urine directly into a selected place of deposit as, for example, a commode in a public lavatory. Though it is anticipated that the invention will be used mostly in public lavatories, it may be used anywhere in an emergency as, for example, in a wooded area where it would be awkward for a woman to remove her panties prior to squatting to relieve herself. With the present invention, the need to squat is entirely eliminated as is the need to remove her panties.

Lastly, the tongs of the present invention may be adapted to serve as a defecation aid. For such use and with reference to FIGS. 7 and 8, a bag 46 is there shown. The bag 46 is closed at its bottom 48 and open at its top 50 and is normally stored flat with a seam 52, open at both ends 54, 56, on either side of the open top 50. Extending from end to end on the inner sides of the bag adjacent its open top are adhesive strips 58, normally covered by parting strips (not shown) which may be removed to enable two strips if facing each other, to be adhered to each other to seal the bag closed after use. Desirably there is another strip 58' is above the strip or strips 58 which may be used to further seal the bag after use. In accordance with the invention a flexible rod 60 is provided which may be bent into a U-shape as seen in FIG. 7 with ends 62, 64 being inserted into the open ends 54 of the seams to extend beyond the opposite open ends 56 of the seams. Integral with the ends of the rod 60 are socket members 66, 67 each having a respective socket 68, 69 adapted to receive the free ends 70, 72 of the tong legs 21, 22. When the legs of the rod 60 are inserted into the seams 52 and the sockets 68, 69 joined to the ends 70, 72 of the tong legs, the over-all length of the bent rod and tongs is such that the user may readily position the bag beneath her anus, open the bag by squeezing the handles together, defecate and thereafter seal the bag closed with the adhesive strips 58 after peeling away the parting strips.

Figure 5:
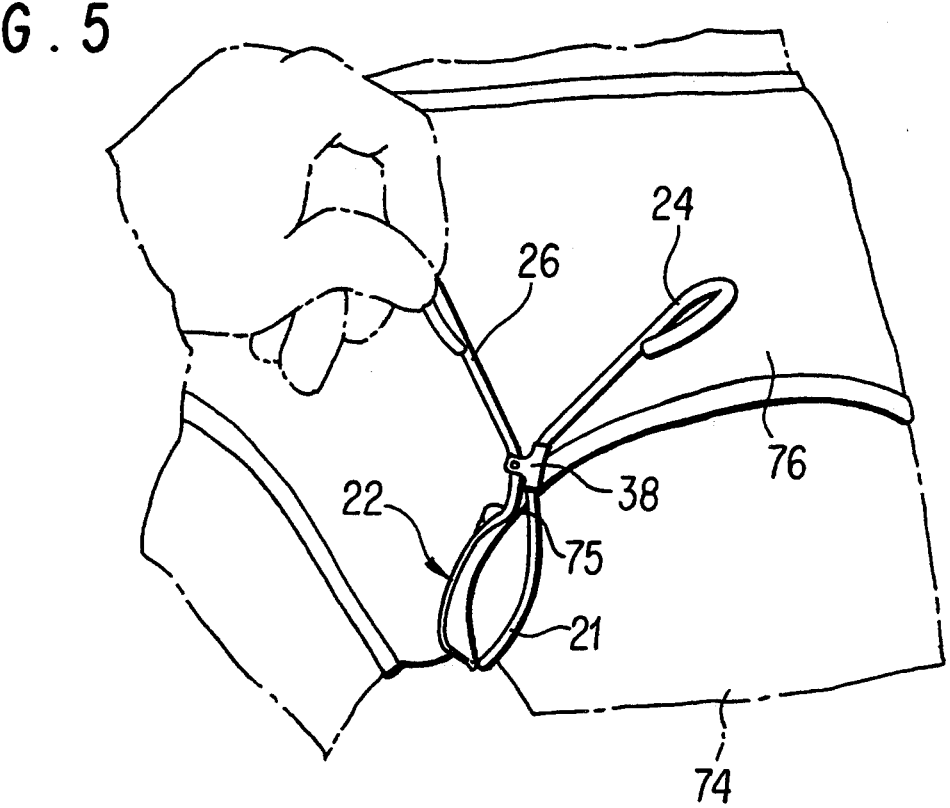
FIG. 5 is a broken perspective view showing how the tongs are initially arranged by a woman wearing panties, the bag being omitted for reasons of clarity.
Figure 6:
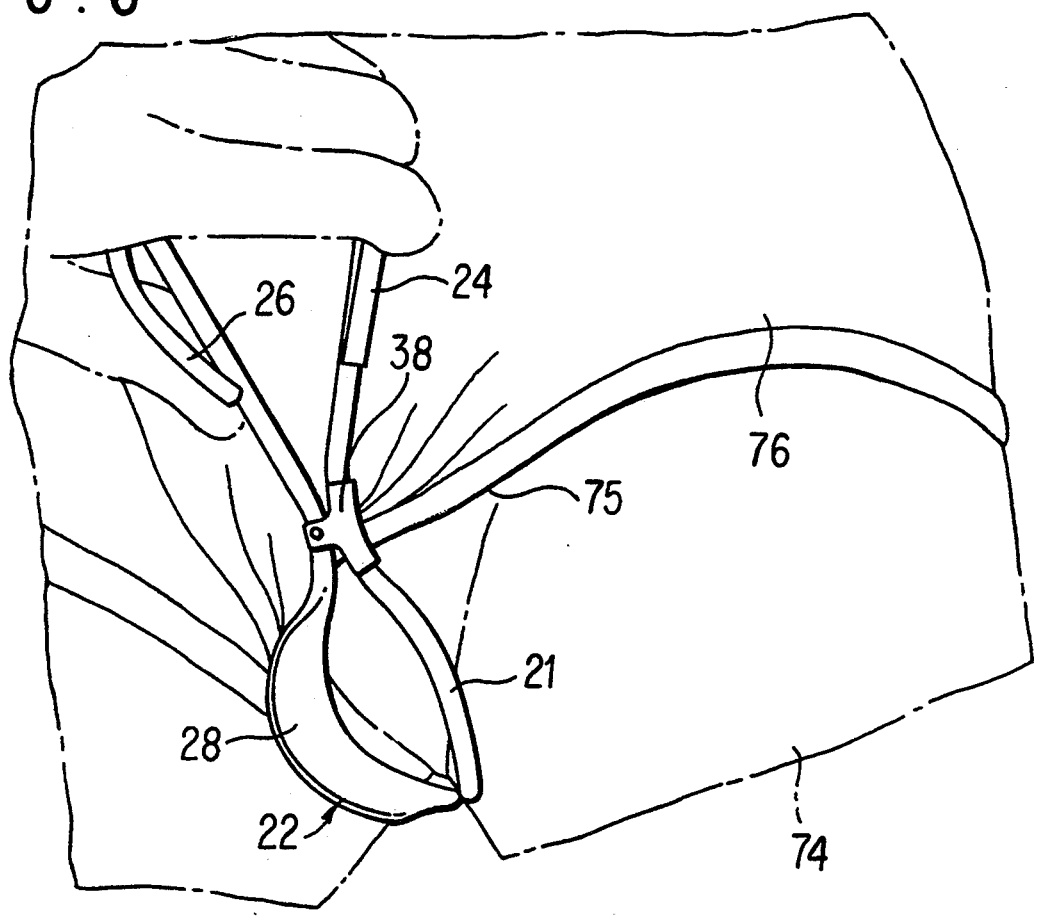
FIG. 6 is a view similar to FIG. 7 but somewhat enlarged to show the hem of the panty hose fully engaged by one leg of the tongs and moved entirely clear of the pubic region.

FIGS. 5 and 6 illustrate the use of the invention by a woman wearing panties. The bag is not illustrated to prevent its interfering with the view but it should be understood that the preferred bag is of clear very flexible plastic material which does not interfere in any way with the operation of the tongs to push the panty hose to one side. As a first step, with the tong legs fully closed, they are inserted between one of the woman's legs 74 and the corresponding leg opening 75 of the panties 76. When the bag is positioned approximately in the correct position from front to back, the user squeezes the tong handles 24, 26 together which spreads the tong legs 21, 22. As can be seen in FIG. 6 the tong leg 21 anchors on the woman's leg 74 thereby providing a reaction for the other leg 22 of the tongs which continues to move to the left in FIG. 6 and in so doing gathers the panty leg material into the bight 36 between the legs 30, 32 of the channel shaped member 28 on the leg 22 of the tongs, see FIG. 4, until the bag is laterally properly position beneath the urinary exit of the woman and with the panty hose material entirely clear of the exit, whereupon the woman relieves herself into the bag without danger of soiling her panties. If the bag has an opening 44 in its lower end (FIG. 1) the bag can be positioned funnel-like, to direct the stream into a receptacle such as a commode.

For defecation, the closed bottom, defecation bag 46, illustrated in FIGS. 7 and 8 is used. Depending on the structure of the panties they can also remain in place and the channel 28 would be effective to push one leg of the panty hose clear of the anus as the tong legs are moved apart to open the defecation bag 46. Upon completion of her bowel movement the woman removes the panties, peels the parting strips from the adhesive strips 58, as explained above, seals the bag and then disposes of it in an acceptable place.

The invention may be used by girls aged five years and up, for example, when in school. Though the invention has been described primarily as useful for females, it may also be useful to males as when traveling long distances or when on watch at sea where no facilities are accessible to a watch station. The invention is also of particular value to men or women who may be incontinent. The tongs and a supply of bags, some open at the bottom some closed, will, with tissue sheets be packaged in one box. The bags may be distinctively colored and one type may be labeled URINE and the other EXCREMENT. Replacement packages of the bags with tissue can be purchased and kept, with the tongs, in a users purse in readiness for use as necessary.

Having now fully described my invention, what I claim is:

1. Aid for use by persons for the elimination of bodily waste comprising, in combination, a first flexible waterproof bag having an adjustable opening at one end, a pair of substantially parallel open ended seams on opposite sides of said opening, tongs comprising a pair of legs having inner ends and free outer ends insertable into open ends of the respective seams on the opposite sides of said bag opening, a handle integral with the inner end of each leg, and a common pivotal connection joining together said legs intermediate the inner ends thereof and said handles, said handles being operable in unison for controlling relative movement of said legs including the free outer ends thereof towards and away from each other about said common pivotal connection for adjusting the size of said bag opening when said legs are received in the respective seams on opposite sides of said bag opening.

2. The aid of claim 1 wherein said bag is funnel shaped so as to be wide at the open end of said bag and narrow at the opposite end of said bag and an aperture in the lower end of said bag enabling liquid contents of said bag to be drained into a selected place of deposit.

3. The aid of claim 1 wherein said handles and legs are relatively movable about said common pivotal connection in opposite directions in substantially a common plane, said common pivotal connection having an axis substantially perpendicular to said substantially common plane.

4. The aid of claim 3 wherein each leg of said tongs and its handle lie on the same side of the axis of said pivotal connection whereby movement of said handles towards each other spreads said legs and vice versa.

5. The aid of claim 3 wherein said legs, handles and pivotal connection are arranged relative to each other that when the outer ends of said legs are positioned to be closer to each other said handles are positioned to be farther from each other and when said legs are positioned to be farther from each other said handles are positioned to be closer to each other.

6. The aid of claim 1 wherein an inner end of one of said legs carries a bracket extending in the direction of the other of said legs, said common pivotal connection being carried by said bracket.

7. The aid of claim 3 including spring means for biasing said legs towards each other and said handles away from each other.

8. The aid of claim 3 wherein one of said legs of said tongs carries an elongated outwardly opening channel which is of inverted L-shaped in cross section one of the legs of said channel being substantially perpendicular to the plane of movement of said tong legs and the other of said legs being substantially parallel to said plane for engagement through a seam of said bag with an edge of a leg opening of a woman's panties to push the same aside as the legs of said tongs are spread apart to open said bag for use.

9. Aid for use by persons in the elimination of bodily waste comprising, in combination, tongs including a pair of relatively moveable legs having pivotally interconnected inner ends and freely extending outer ends, manually operable means for controlling movement of said legs towards and away from each other, a bag closed at one end and open at the other, seams on opposite sides of the open end of said bag, each seam having a pair of open ends, a flexible U-shaped rod received in said seams and having exposed ends extending freely from the open ends of said seams, a pair of sockets carried by the respective extending ends of said rods, each of said sockets being releasably connectable with the freely extending outer ends of the legs of said tongs, the combined length of said tongs with said rod attached thereto being selected to enable the location of the open end of said bag beneath the anus of a user to receive bodily waste derived from a bowel movement of said user.

* * * * *

UNITED STATES PATENT AND TRADEMARK OFFICE
CERTIFICATE OF CORRECTION

PATENT NO. : 5,353,805
DATED : October 11, 1994
INVENTOR(S) : Gregory L. Mojena

It is certified that error appears in the above-indentified patent and that said Letters Patent is hereby corrected as shown below:

On the title page: Item

[76] Inventor: Gregory L. Mojena, Calle 10, B7-1, Sabana Gardens, Carolina, Puerto Rico Signed and Sealed this Twentieth Day of December, 1994

Attest:

BRUCE LEHMAN

Attesting Officer

Commissioner of Patents and Trademarks